United States Patent
Funaba et al.

(10) Patent No.: US 6,555,529 B1
(45) Date of Patent: Apr. 29, 2003

(54) REMEDIES FOR INTRAMEDULLARY DISEASES

(75) Inventors: Yuriko Funaba, Kamakura (JP); Junzo Koike, Fujisawa (JP); Masahiko Tanahashi, Takatsuki (JP); Seiji Okazaki, Kamakura (JP); Masatoshi Ito, Yokohama (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/380,090

(22) PCT Filed: Dec. 24, 1998

(86) PCT No.: PCT/JP98/05878

§ 371 (c)(1),
(2), (4) Date: Aug. 25, 1999

(87) PCT Pub. No.: WO99/33473

PCT Pub. Date: Jul. 8, 1999

(30) Foreign Application Priority Data

Dec. 25, 1997 (JP) .............................................. 9-358245

(51) Int. Cl.⁷ .............................................. A61K 31/66
(52) U.S. Cl. ...................................................... 514/108
(58) Field of Search ........................................ 514/108

(56) References Cited

U.S. PATENT DOCUMENTS 5,403,829 A * 4/1995 Lehtinen et al. ............ 514/108

FOREIGN PATENT DOCUMENTS

| WO | 93 24498 | 12/1993 |
| WO | 96 39150 | 12/1996 |
| WO | 97 04785 | 2/1997 |
| WO | 97 33552 | 9/1997 |

* cited by examiner

*Primary Examiner*—Theodore J. Criares
(74) *Attorney, Agent, or Firm*—Birch, Stewart,. Kolasch & Birch, LLP

(57) ABSTRACT

The present invention has the objective of offering drug for treating abnormalities in bone marrow which corrects the biological balance in the bone marrow, in particular which has the effect of suppressing inflammatory cell infiltration and suppressing cell growth-differentiation factor increase.

The present invention relates to drug for treating abnormalities in bone marrow which has, as an effective component, a methanebisphosphonic acid derivative, ester thereof, medicinally acceptable salt thereof, or a hydrate of these.

The methanebisphosphonic acid derivatives of the present invention show an outstanding bone marrow abnormality therapeutic effect, so efficacy can be expected in the prevention and treatment of rheumatoid arthritis, multiple myeloma, osteomyelitis and other bone marrow abnormalities. Furthermore, application can also be expected in the prevention and treatment of hypoplastic anaemia, myelocytic leukaemia and other such haematopoietic disorders.

5 Claims, No Drawings

REMEDIES FOR INTRAMEDULLARY DISEASES

This is the national phase under 35 U.S.C. §317 of PCT International Application No. PCT/JP98/05878 which has an International filing date of Dec. 24, 1998, which designated the United States of America.

TECHNICAL FIELD

This invention relates to a drug for treating abnormalities in bone marrow which cures abnormalities in the bone marrow.

TECHNICAL BACKGROUND

The bone marrow is an organ responsible for part of haematopoiesis, and since it is in contact with the medullary cavity and cancellus bone it is possible that, as a result of bone marrow abnormalities, there will occur abnormalities in the bone and other surrounding tissues, and serious illness will be exhibited. The bone marrow abnormalities referred to here are defined as those where general abnormality of the biological balance in the bone marrow is indicated, such as viral and bacterial infections in the bone marrow, cellular infiltration of the bone marrow, abnormalities of the bone marrow haematopoiesis, proliferation of malignant neoplasms in the bone marrow and concentration changes in cell growth-differentiation factors.

For example, the inflammation of the bone and bone marrow which is brought about by many pathogenic factors such as pyogenic bacteria, tuberculosis, syphilis, fungi and specified viruses or exogenous matter is termed osteomyelitis and, when there is osteomyelitis, as a result of the impeded blood circulation and infiltration of neutrophils into the bone marrow region, there occur surrounding bone decalcification and tissue breakdown, with resulting pain. While the occurrence of acute osteomyelitis is declining due to the widespread use of antibiotics, as a result of for example the appearance of resistant microorganisms, osteomyelitis which from the outset follows a subacute or chronic course remains a problem [Green, N. E. et al., J. Bone Joint Serg., 63-A, p107–114 (1981)].

In rheumatoid arthritis, it has been reported that there is an increase in the concentration of components which induce a proliferation of synoviocytes in the bone marrow and, moreover, that abnormal myelocytes are found within the bone marrow and changes in cell ratios such as an increase in the T cell ratio are shown [Ochi, T., Igaku no Ayumi, 161, p609–613 (1992)]. Since myelocytes differentiate into neutrophils, it can be expected that the number of neutrophils showing abnormal activity will increase in the bone marrow and contribute to an aggravation of the condition. Moreover, since the progress of a condition where marked changes in the bone marrow are exhibited is rapid and the outlook for the patient is severe [Ochi, T. et al., Arthritis Rheum., 31, p37 (1988)], there is the possibility that early stage improvement in the pathological changes in the bone marrow could be linked to the cure of the disease. In addition, in the treatment of rheumatoid arthritis there is also the problem that there is a considerable likelihood of multiple agents which show serious side effects being used concomitantly, such as steroids which display a variety of adverse-side effects and gold preparations compounds which exhibit hematopoiesis decrease.

In leukaemia, irrespective of cell type and whether it is acute or chronic, or whether it is myelogenicor lymphocytic leukaemia, the bone marrow is the location of a markedly increased production of leukaemia cells, and normal blood components decline. Again, in multiple myeloma, a principal feature is the proliferation of tumours of plasma cells, which are cells at the end of the B cell lineage, and a multiplicity of these is produced in the bone marrow at sites of active haematopoiesis. In leukaemia, multiple myeloma and the like, an increase in cell growth-differentiation factor activity in the bone marrow and an abnormal proliferation of cells are found, and the abnormalities in the biological balance in the bone marrow are believed to be closely connected with the presentation and continuance of the diseased state. Furthermore, hematopolesis decrease is widely known to be a adverse-side effect of the chemotherapeutic agents used in treatment, and even with therapy by homologous bone marrow transplantation the transplantation results are imperfect and carry the risk of subsequent recurrence.

Thus, inflammatory cell infiltration into the bone marrow, abnormal cell proliferation or an abnormal increase in cell growth-differentiation factor activity in the bone marrow are closely related with many bone marrow abnormalities, and the development of drugs based on a hitherto unavailable novel mechanism of action is desired so as to correct the biological balance in the bone marrow and treat bone marrow abnormalities. Now, the aforementioned disorders in which bone marrow abnormalities are shown have just been given as examples, and there are no restrictions thereto.

Bisphosphonic acid compounds suppress excessive bone resorption in tumour-induced osteolysis, Paget disease and osteoporosis, and some have already been used for medical treatment. These compounds are disclosed in, for example, EP177443, EP337706, AU8551534, EP317505, EP27982 and EP94714.

Furthermore, in EP100718, U.S. Pat. No. 4,234,645, EP84822, WO9203451 and WO935052, bisphosphonic acid compounds with an anti-inflammatory action are disclosed. However, the anti-inflammatory effects described therein form a basis for the treatment of skeletal system disorders such as arthritis, osteoarthritis and ankylosing spondylitis.

In relation to the anti-inflammatory action of bisphosphonic acid compounds, the effects on for example arthritic model rats have been pathologically analysed [Flora, L. et al., Arthritis and Rheumatism, 22, p340–346 (1979)] but no investigations relating to bone marrow changes have been carried out.

Again, in WO97/49711 and WO97/04785 for example, bisphosphonic acid compounds have been disclosed which exhibit an antitumour action and, moreover, it has also been reported that bisphosphonic acid compounds exhibit antitumour actions by inhibiting cell growth [Claire, M. et al., Br. J. Haematol., 98, p665 (1997)], [Knamori, M. et al., J. Exp. Cancer Res., 16, p39 (1997)]. However, depending on the particular compound, there are also examples which cause an increase in tumour growth [Kostenik, P. J. et al., Cancer Res., p5452 (1993)], so an antitumour action is not a characteristic common to the bisphosphonic acid structure.

In U.S. Pat. No. 4,067,971, there is disclosed a bisphosphonic acid compound used for the treatment of hypoxia and ischemic tissue disease but this compound depends on an oxygen-releasing action from red blood cells and it does not correct abnormalities of red blood cell formation. in the bone marrow.

Thus, it is already known that many bisphosphonic acid compounds have a bone resorption suppression effect, an anti-inflammatory effect and an anti-rheumatic effect, and that some bisphosphonic acid compounds exhibit an antitumour effect and show efficacy in the treatment of hypoxia. However, no findings have hitherto been obtained to indicate that bisphosphonic acid compounds are effective in the treatment of bone marrow abnormalities.

DISCLOSURE OF THE INVENTION

The present invention aims to offer a drug which, by correcting bone marrow abnormalities as exemplified above, is effective in the treatment of bone marrow diseases.

As a result of painstaking research conducted with this objective, the present inventors have discovered that the methanebisphosphonic acid derivatives represented by general formula (I) below, and salts thereof, have the effect of correcting the biological balance in the bone marrow, in particular suppressing inflammatory cell infiltration and suppressing cell growth-differentiation factor increase, and have efficacy in the treatment of bone marrow abnormalities. The present invention has been perfected based on this discovery.

In order to realise the aforesaid objective, the present invention has the following constitution. Specifically, the present invention relates to a bone marrow abnormality treatment agent in which the effective component is a methanebisphosphonic acid derivative represented by general formula (I):

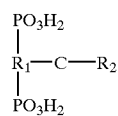

[I]

[where, in the formula, (a) $R_1$ is hydrogen, and $R_2$ is Ar—X—, Het—X—, Ar—X—A—, Het-X—A—, Ar—X—A—N($R_3$)—, Het—X—A—N($R_3$)— (here Ar is an unsubstituted or substituted aryl, Het is an unsubstituted or substituted monocyclic 5- or 6-membered monoaza, diaza or thiaza aryl which is bonded via a ring carbon atom, X is S, O or NH, A is alkylene and $R_3$ is hydrogen or a lower alkyl) or N-phenylthiocarbamoyl, or (b) $R_1$ is hydrogen or hydroxy, and $R_2$ is $R_4$—A— (here A is alkylene, $R_4$ is hydrogen, Ar (Ar has the same meaning as above), an unsubstituted or substituted monoaza, diaza or thiaza aryl which is bonded via a ring carbon atom or ring nitrogen atom, a mono- or di-substituted amino (the substituent groups being alkyl, Ar-alkyl, Ar—X-alkyl (X represents S or O) or Het-alkyl, and may be the same or different, but excluding the case of dialkyl; Ar and Het have the same meanings as above), or Ar-substituted alkyleneamino (Ar has the same meaning as above))], or ester thereof, medicinally acceptable salt thereof, or a hydrate of these.

Optimum Mode for Practising the Invention

The present invention relates to the use, for the treatment of bone marrow abnormalities, of the methanebisphosphonic acid derivatives of formula (I)

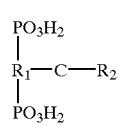

[I]

[where, in the formula, (a) $R_1$ is hydrogen, and $R_2$ is Ar—X—, Het—X—, Ar—X—A—, Het—X—A—, Ar—X—A—N($R_3$)—, Het—X—A—N($R_3$)— (here Ar is an unsubstituted or substituted aryl, Het is an unsubstituted or substituted monocyclic 5- or 6-membered monoaza, diaza or thiaza aryl which is bonded via a ring carbon atom, X is S, O or NH, A is alkylene and $R_3$ is hydrogen or a lower alkyl) or N-phenylthiocarbamoyl, or (b) $R_1$ is hydrogen or hydroxy, and $R_2$ is $R_4$—A— (here A is alkylene, $R_4$ is hydrogen, Ar (Ar has the same meaning as above), an unsubstituted or substituted monoaza, diaza or thiaza aryl which is bonded via a ring carbon atom or ring nitrogen atom, a mono- or di-substituted amino (the substituent groups being alkyl, Ar-alkyl, Ar—X-alkyl (X represents S or O) or Het-alkyl, and may be the same or different, but excluding the case of dialkyl; Ar and Het have the same meanings as above), or Ar-substituted alkyleneamino (Ar has the same meaning as above))], or esters thereof, medicinally acceptable salts thereof, or hydrates of these.

The unsubstituted aryl represented by Ar is phenyl, while the substituted aryl is phenyl which is mono- or poly-substituted, for example di- or tri-substituted, with for example a lower alkyl (optionally substituted with an amino, lower alkylamino, di-lower alkylamino or tri-lower alkylsiloxy), lower alkenyl (optionally substituted with an amino, lower alkylamino, di-lower alkylamino or tri-lower alkylsiloxy), $C_{3-8}$ cycloalkyl (optionally substituted with an amino, lower alkylamino, di-lower alkylamino or tri-lower alkylsiloxy), lower alkoxy (optionally substituted with an amino, lower alkylamino, di-lower alkylamino or tri-lower alkylsiloxy), lower alkylthio (optionally substituted with an amino, lower alkylamino, di-lower alkylamino or tri-lower alkylsiloxy), trifluoromethyl, halogen and/or phenyl (optionally substituted with a lower alkyl, lower alkoxy, lower alkylthio, trifluoromethyl or halogen).

The monocyclic 5- or 6-membered monoaza aryl, diaza aryl or thiaza aryl is for example pyrrolyl, imidazolyl, including 1-, 2-, 4-or 5-imidazolyl, pyrazolyl, including 1- or 3-pyrazolyl, thiazolyl, including 2- or 4-thiazolyl, or pyridyl, including 2-, 3- or 4-pyridyl. Said groups can be substituted with one or more than one alkyl group. Preferred examples of substituted such groups include lower alkyl-substituted-1-imidazole and -5-imidazole, 5-lower alkyl-2-thiazolyl, for example 5-methyl-2-thiazolyl or 5-ethyl-2-thiazolyl, and lower alkyl-substituted 2- and 3-pyridyl.

The unsubstituted or substituted monocyclic 5- or 6-membered monoaza aryl, diaza aryl or thiaza aryl which is bonded via a ring carbon atom, and which is denoted by Het, is preferably a radical selected from the group comprising 2-, 4- and 5-imidazolyl, 3-pyrazolyl, 4-thiazolyl and 2-, 3- and 4-pyridyl, and it may be unsubstituted or lower alkyl-substituted.

The unsubstituted or substituted monocyclic 5- or 6-membered monoaza aryl, diaza aryl or thiaza aryl, which is bonded via a ring carbon atom or ring nitrogen atom, is preferably a radical selected from the group comprising pyrrolyl, imidazolyl, pyrazolyl, thiazolyl and pyridyl, and it may be unsubstituted or lower alkyl-substituted.

The unsubstituted or substituted bicyclic monoaza aryl, diaza aryl or thiaza aryl, which is bonded via a ring carbon atom or ring nitrogen atom, is for example an imidazo[1,2-a]pyridyl, preferably imidazo[1,2-a]pyridin-3-yl.

Alkyl is preferably a lower alkyl; the alkylene is preferably a lower alkylene; Ar-alkyl is for example a phenyl-lower alkyl, and substitution within the phenyl ring thereof is possible, as described above.

The amino which is mono- or di-substituted by means of alkyl, Ar-alkyl, Ar-O-alkyl, Ar-S-alkyl or Het-alkyl is preferably phenyl lower alkylamino, N,N-diphenyl lower alkylamino, N-phenoxy lower alkylamino, N-phenoxy lower alkyl-N-lower alkylamino, N-phenoxy lower alkyl-N-phenyl lower alkylamino, N,N-diphenoxy lower alkylamino, N-phenylthio lower alkylamino, N-phenylthio lower alkyl-N-lower alkylamino, N-phenylthio lower alkyl-N-phenyl lower alkylamino, N,N-diphenylthio lower alkylamino, N-pyridyl lower alkyl-N-lower alkylamino, N-pyridyl lower alkyl-N-phenyl lower alkylamino, N-phenoxy lower alkyl-N-pyridyl lower alkylamino, N-phenylthio lower alkyl-N-pyridyl lower alkylamino or N,N-dipyridyl lower alkylamino, and the phenyl or pyridyl moiety thereof may also be substituted as described above.

Ar-substituted alkyleneamino is preferably a substituted $C_{4-6}$ cyclic amino, for example 1,4-butyleneamino (that is to say pyrrolidin-1-yl) or 1,5-pentyleneamino (that is to say piperidin-1-yl), or a lower alkyleneamino, which is substituted by means of a phenyl group (the phenyl group may also itself be substituted), for example 2-(4-chlorophenyl)-1,4-butyleneamino or 3-phenyl-1,5-pentyleneamino.

Halogen indicates, for example, fluoro, chloro or bromo, and preferably chloro, but it may also be iodo.

Where a group or compound is modified by means of the term 'lower', this indicates that it may contain up to seven carbon atoms.

Lower alkyl includes, for example, methyl, ethyl, n-propyl, isopropyl, n-butyl, isobutyl, sec- and tert-butyl, and also the corresponding pentyl and hexyl groups. A $C_1$ to $C_4$ alkyl is preferred.

Lower alkenyl is, for example, vinyl, 1-propenyl, allyl, 1-butenyl, 2-butenyl, 3-butenyl or the like. A $C_2$ to $C_4$ alkenyl is preferred.

$C_3$ to $C_8$ cycloalkyls are, for example, cyclopropyl, cyclobutyl, cyclopentyl, cyclohexyl, cycloheptyl and cyclooctyl, with cyclopentyl or cyclohexyl being preferred.

Lower alkoxy includes, for example, methoxy, ethoxy, n-propoxy, isopropoxy and n-butoxy, and also the corresponding pentoxy and hexoxy groups. A $C_1$ to $C_4$ alkoxy is preferred.

Lower alkylthio refers to, for example, methylthio, ethylthio, n-propylthio, isopropylthio and n-butylthio, with a $C_1$ to $C_4$ alkylthio being preferred.

Lower alkylene is a straight chain or branched $C_1$ to $C_7$ alkylene, such as for example methylene, ethylene, propylene, butylene, pentylene, hexylene, heptylene, 2-methyl-1,3-propylene, 2,4-or 1,5-dimethyl-1,5-pentylene. The lower alkylene which is a substituent group in the case where $R_3$ is a di-substituted amino will have at least two carbon atoms and preferably contain from 4 to 6 carbon atoms.

For the treatment of bone marrow abnormalities, the present invention relates in particular to the use of methanebisphosphonic acid derivatives where, in formula (I), (a) $R_1$ is hydrogen and $R_2$ is Ar—S—, Ar—O—, Ar—NH—, Het—NH—, Het—S—, Ar—S—A—, Ar—S—A—NH— or Het—S—A—NH— (here Ar is phenyl (which may also be substituted with a lower alkyl, lower alkylthio, trifluoromethyl or halogen), Het is thiazolyl (which may also be substituted with a lower alkyl) or pyridyl (which may also be substituted with a lower alkyl), and A is a lower alkylene) or N-phenylthiocarbamoyl, or (b) $R_1$ is hydrogen or hydroxy, and $R_2$ is $R_4$—A— (here A is lower alkylene and $R_4$ is hydrogen, unsubstituted or lower alkyl-substituted imidazolyl, pyridyl or imidazo[1,2-a]pyridyl bonded via a ring carbon atom or ring nitrogen atom, mono- or di-substituted amino (the substituent groups being lower alkyl, Ar-lower alkyl, Ar-O-lower alkyl, Ar-S-lower alkyl or pyridyl-lower alkyl, and may be the same or different, although the dialkyl case is excluded; Ar represents phenyl (which may be substituted with a lower alkyl, lower alkylthio, trifluoromethyl or halogen), or an Ar-substituted $C_{4-6}$ alkyleneamino (Ar represents phenyl (which may be substituted with a lower alkyl, lower alkylthio, trifluoromethyl or halogen)), and the esters thereof, medicinally acceptable salts thereof, and the hydrates of these.

For the treatment of bone marrow abnormalities, the present invention also relates in particular to the use of methanebisphosphonic acid derivatives where, in formula (I), (a) $R_1$ is hydrogen and $R_2$ is unsubstituted or halogen-substituted phenylthio, lower alkyl-substituted phenylthio, lower alkylthio-substituted phenylthio, unsubstituted or halogen-substituted phenoxy, lower alkyl-substituted phenoxy, lower alkoxy-substituted phenoxy, lower alkylthio-substituted phenoxy, unsubstituted or halogen-substituted phenylamino, lower alkyl-substituted phenylamino, lower alkoxy-substituted phenylamino, lower alkylthio-substituted phenylamino, unsubstituted or lower alkyl substituted thiazolylamino, pyridylthio or N-phenylthiocarbamoyl, or (b) $R_1$ is hydrogen or hydroxy, and $R_2$ is $R_4$—A— (here A is a $C_{1-7}$ alkylene and $R_4$ is an unsubstituted or lower alkyl-substituted imidazolyl, pyridyl or imidazo[1,2-a]pyridyl bonded via a ring carbon atom or ring nitrogen atom), or (c) $R_1$ is hydroxy, and $R_2$ is $R_5$—A— (here A is a $C_{1-7}$ alkylene and $R_5$ is hydrogen, N-phenyl($C_{1-4}$ alkyl)—N—($C_{1-4}$ alkyl)amino, N-phenoxy($C_{1-4}$ alkyl)—N—($C_{1-4}$ alkyl)amino, N-phenylthio($C_{1-4}$ alkyl)—N—($C_{1-4}$ alkyl)amino, N-pyridyl-($C_{1-4}$ alkyl)-N—($C_{1-4}$ alkyl)amino or phenyl-substituted $C_{4-6}$ cyclic amino (the phenyl group may also itself be substituted), and the esters thereof, medicinally acceptable salts thereof, and the hydrates of these.

For the treatment of bone marrow abnormalities, the present invention preferably relates in particular to the use of methanebisphosphonic acid derivatives where, in formula (I), (a) $R_1$ is hydrogen, and $R_2$ is an unsubstituted or chloro-substituted phenylthio, $C_{1-4}$ alkyl-substituted phenylthio, $C_{1-4}$ alkylthio-substituted phenylthio, unsubstituted or chloro-substituted phenoxy, $C_{1-4}$ alkyl-substituted phenoxy, $C_{1-4}$ alkoxy-substitutedphenoxy, $C_{1-4}$ alkylthio-substituted phenoxy, unsubstituted or chloro-substituted phenylamino, $C_{1-4}$ alkyl-substituted phenylamino, $C_{1-4}$ alkoxy-substituted phenylamino, $C_{1-4}$ alkylthio-substituted phenylamino, unsubstituted or $C_{1-4}$ alkyl-substituted thiazolylamino, phenylthio or 2-pyridylthio-substituted $C_{1-4}$ alkylamino, 2-, 3- or 4-pyridylthio, or N-phenylthiocarbamoyl, or (b) $R_1$ is hydrogen or hydroxy, and $R_2$ is $R_4$—A— (here A is methylene, ethylene, propylene or pentylene, $R_4$ is imidazol-1-yl, imidazol-4-yl, imidazol-5-yl, 1-methylimidazol-2-yl, 5-methylimidazol-2-yl, 4-methylimidazol-5-yl, 2- or 3-pyridyl, or imidazo[1,2-a]pyridyl-3-yl), or (c) $R_1$ is hydroxy, and $R_2$ is $R_5$—A— (here A is methylene, ethylene, propylene or pentylene, $R_5$ is hydrogen, N-methyl-N-(2-phenylethyl)amino, N-methyl-N-(3-phenylpropyl)amino, N-methyl-N-(5-phenylpentyl)amino, N-methyl-N-(2-phenoxyethyl)amino, N-methyl-N-(3-phenoxypropyl)amino, N-methyl-N-(2-phenylthioethyl)amino, N-methyl-N-(3-phenylthiopropyl)amino, N-methyl-N-[2-(3-pyridyl)ethyl]amino, N-methyl-N-[3-(2-pyridyl)propyl]amino, 4-phenylpiperidin-1-yl, 4-phenylpiperidin-2-yl, 3-(4-chlorophenyl)pyrrolidin-1-yl or 3-(4-chlorophenyl)pyrrolidin-2-yl),
and the esters thereof, medicinally acceptable salts thereof, and the hydrates of these.

Amongst the compounds of the present invention, particularly desirable for the treatment of bone marrow abnormalities are the methanebisphosphonic acid derivatives represented by general formula (Ia):

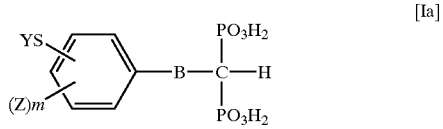

[Ia]

[where, in the formula, B represents —X—(CH$_2$)$_n$— (n is an integer in the range 0 to 6); X represents S, O or NH; Y represents a straight chain or branched chain lower alkyl comprising from 1 to 6 carbon atoms (which may also be substituted with an amino group, lower alkylamino group, di-lower alkylamino group or tri-lower alkylsiloxy group) or phenyl (which may also be substituted with a lower alkyl, lower alkoxy, lower alkylthio, trifluoromethyl or halogen), Z denotes a lower alkyl group, trifluoromethyl group, lower alkenyl group, lower alkoxy group, lower alkylthio group or C$_{3-8}$ cycloalkyl group, and m represents an integer in the range 0 to 2], and preferred are methanebisphosphonic acid derivatives selected from 1-hydroxyethane-1,1-bisphosphonic acid, 3-[N-(3-phenylpropyl)-N-methylamino]-1-hydroxypropane-1,1-bisphosphonic acid, 3-[N-(5-phenylpentyl)-N-methylamino]-1-hydroxypropane-1,1-bisphosphonic acid, 3-[N-3-(2-pyridyl)propylamino]-1-hydroxypropane-1,1-bisphosphonic acid, 3-[N-(3-phenoxypropyl)-N-methylamino]-1-hydroxypropane-1,1-bisphosphonic acid, 3-[N-(2-phenoxyethyl)-N-methylamino]-1-hydroxypropane-1,1-bisphosphonic acid, 4-(4-phenylpiperidin-1-yl)-1-hydroxybutane-1,1-bisphosphonic acid, 3-[3-(4-chlorophenyl)pyrrolidin-1-yl]-1-hydroxypropane-1,1-bisphosphonic acid, 2-(imidazol-1-yl)-1-hydroxyethane-1,1-bisphosphonic acid, 2-(imidazol-2-yl)-1-hydroxyethane-1,1-bisphosphonic acid, 2-(imidazol-4-yl)-1-hydroxyethane-1,1-bisphosphonic acid, 2-(imidazol-5-yl)-1-hydroxyethane-1,1-bisphosphonic acid, 3-(imidazol-4-yl)-1-hydroxypropane-1,1-bisphosphonic acid, 2-(1-methylimidazol-2-yl)-1-hydroxyethane-1,1-bisphosphonic acid, 2-(4-methylimidazol-5-yl)-1-hydroxyethane-1,1-bisphosphonic acid, 2-(3-pyridyl)-1-hydroxyethane-1,1-bisphosphonic acid, 2-(2-pyridyl)ethane-1,1-bisphosphonic acid, [(5-n-butyl-2-thiazolyl)amino]methane-1,1-bisphosphonic acid, [(5-methyl-2-thiazolyl)amino]methane-1,1-bisphosphonic acid, [(2-thiazolyl)amino]methane-1,1-bisphosphonic acid, (2-pyridylthio)methane-1,1-bisphosphonic acid, 3-[N-(2-phenylthioethyl)-N-methylamino]-1-hydroxypropane-1,1-bisphosphonic acid, 3-[N-(3-phenylthiopropyl)-N-methylamino]-1-hydroxypropane-1,1-bisphosphonic acid, 3-(pyrrolidin-1-yl)-1-hydroxypropane-1,1-bisphosphonic acid, 2-(piperidin-1-yl)-1-hydroxyethane-1,1-bisphosphonic acid, [N-(4-phenylthiobutyl)-amino]methane-1,1-bisphosphonic acid, [N-[4-(2-pyridylthio)butyl]amino]methane-1,1-bisphosphonic acid, (N-phenylaminothiocarbonyl)methane-1,1-bisphosphonic acid, 2-(imidazo[1,2-a]pyridin-3-yl)-1-hydroxyethane-1,1-bisphosphonic acid, phenoxymethane-1,1-bisphosphonic acid, thiomorpholinomethane-1,1-bisphosphonic acid, (4-chlorophenylthio)methane-1,1-bisphosphonic acid and (4-methylthiophenylthio)methane-1,1-bisphosphonic acid.

An especially preferred embodiment of the present invention is a compound selected from 1-hydroxyethane-1,1-bisphosphonic acid, 2-(imidazol-1-yl)-1-hydroxyethane-1,1-bisphosphonic acid, 2-(3-pyridyl)-1-hydroxyethane-1,1-bisphosphonic acid, 2-(2-pyridyl)ethane-1,1-bisphosphonic acid, (4-chlorophenylthio)methane-1,1-bisphosphonic acid, (4-methylthiophenylthio)methane-1,1-bisphosphonic acid, 3-[N-(2-phenylthioethyl)-N-methylamino]-1-hydroxypropane-1,1-bisphosphonic acid, 3-(pyrrolidin-1-yl)-1-hydroxypropane-1,1-bisphosphonic acid, (N-phenylaminothiocarbonyl)methane-1,1-bisphosphonic acid and 2-(imidazo[1,2-a]pyridin-3-yl)-1-hydroxyethane-1,1-bisphosphonic acid, the medicinally acceptable salts thereof and hydrates of these.

The medicinally acceptable salts of the compounds of formula (I) are the salts with bases, preferably the alkali metal salts such as the potassium and sodium salts, the alkaline earth metal salts such as the calcium and magnesium salts, or the ammonium salts with ammonia or with organic amines.

The aforesaid methanebisphosphonic acid derivatives are already known or can be manufactured by methods which are themselves known. Thus, for example, the compounds of formula (I) where R$_1$ is hydrogen and R$_2$ is Ar—S— can be obtained by reacting a tetra lower alkyl methanebisphosphonate with a disulphide of formula Ar—S—S—Ar in the presence of a strong base, for example NaH, and then subjecting the tetra lower alkyl ester obtained to hydrolysis.

The compounds corresponding to formula (I) in which R$_1$ is hydrogen and R$_2$ is Het—NH— can be obtained, for example, by reacting a mixture of H$_3$PO$_3$ and PHal$_3$ (here Hal is a halogen, preferably chloro) with a formyl amide of formula Het—NH—CHO, or by heating the amine Het—NH$_2$ along with a lower alkyl orthoformate and di-lower alkyl phosphite, and then subjecting the reaction product to, for example, acid hydrolysis.

The compounds of formula (I) in which R$_1$ is a hydroxyl group and R$_2$ is amino-A— are disclosed in DE-OS-2405254. The production of compounds of formula (I) where R$_1$ is hydrogen and R$_2$ is Ar—S—A—N(R$_3$)— or Het—S—A—N(R$_3$)— is disclosed in, for example, EP-A-464509.

Where the methanebisphosphonic acid derivatives relating to the present invention are to be used in the treatment of bone marrow abnormalities, they may be offered for use as they are or in the form of medicinal compositions mixed with known pharmaceutically acceptable carriers, excipients and the like.

Administration may be by oral administration in the form of tablets, capsules, powders, granules, pills or the like, or by parenteral administration in the form of an injection, syrup, ointment, suppository or the like. The dose will differ according to the patient, administration route and symptoms, etc, but will lie in the range about 0.1 mg to 5 g and preferably about 1 mg to 2 g, with this amount being administered orally or perenterally once per day or divided-up for administration a number of times per day.

Below, the present invention is explained in still more specific terms by providing examples.

EXAMPLE 1

Suppression of Osteomyelitis Accompanying Rat Adjuvant Arthritis

The following pharmacological tests were performed using (4-methylthiophenyl)thiomethanebisphosphonic acid disodium salt as the test compound (hereinafter referred to as Compound 1).

0.1 mg of inactivated dried Mycobacterium butyricum was suspended in 0.1 ml of liquid paraffin, and this was injected into the left hind foot pad of 8-week old female Lewis rats. Compound 1 was dissolved in sterile distilled water as the solvent, and subcutaneous administration was carried out every day for 2 weeks at a dose of 2.5 mg per kg bodyweight starting 1 week (day 8) after the day of the adjuvant treatment (day 1).

As a control group, the subcutaneous administration of sterile distilled water was carried out. One day after the completion of the administration (day 22) the rats were sacrificed, the skin and muscle removed from the right hind limb and, following decalcification, pathological specimens were prepared. These were observed under a microscope and, using neutrophil infiltration into the talocrural joints and intertarsal and tarsometatarsal joints as an index, the severity of osteomyelitis was scored as one of four grades, 0, 1, 2 or 3, and evaluation carried out.

In addition to Compound 1, there were used as test compounds 4-amino-1-hydroxybutane-1,1-bisphosphonic acid (Compound 2) and 2-(3-pyridyl)-1-hydroxyethane-1,1-bisphosphonic acid (Compound 3). Furthermore, Diclofenac (Compound 4) and Indomethacin (Compound 5) were used as existing anti-inflammatory drugs. The results obtained are shown in Table 1 as mean values±standard errors.

Using the Dannett multiple comparison method (parametric), the results were assigned the symbol * when significant at a level of significance of $p<0.05$, and the symbol ** when significant at a level of significance of $p<0.01$, compared to the control group in which only sterile distilled water was used.

TABLE 1-1

|  | No. of animals | Osteomyelitis score for the talocrural joint region | Osteomyelitis score for the intertarsal and tarsometatarsal joints |
|---|---|---|---|
| Administration of sterile distilled water only | 6 | 2.0 ± 0.0 | 2.2 ± 0.31 |
| Compound 1 (2.5 mg/kg) | 6 | 0.2 ± 0.17** | 0.2 ± 0.17** |

TABLE 1-2

|  | No. of animals | Osteomyelitis score for the talocrural joint region | Osteomyelitis score for the intertarsal and tarsometatarsal joints |
|---|---|---|---|
| Administration of sterile distilled water only | 6 | 1.7 ± 0.49 | 1.7 ± 0.21 |
| Compound 2 (0.31 mg/kg) | 6 | 0.0 ± 0.0** | 0.2 ± 0.17** |

TABLE 1-3

|  | No. of animals | Osteomyelitis score for the talocrural joint region | Osteomyelitis score for the intertarsal and tarsometatarsal joints |
|---|---|---|---|
| Administration of sterile distilled water only | 6 | 2.3 ± 0.49 | 2.5 ± 0.22 |
| Compound 3 (0.31 mg/kg) | 6 | 0.0 ± 0.0** | 0.0 ± 0.0** |

TABLE 1-4

|  | No. of animals | Osteomyelitis score for the talocrural joint region | Osteomyelitis score for the intertarsal and tarsometatarsal joints |
|---|---|---|---|
| Administration of sterile distilled water only | 6 | 1.5 ± 0.3 | 1.8 ± 0.2 |
| Compound 4 (0.1 mg/kg) | 6 | 1.2 ± 0.3 | 1.8 ± 0.2 |

TABLE 1-5

|  | No. of animals | Osteomyelitis score for the talocrural joint region | Osteomyelitis score for the intertarsal and tarsometatarsal joints |
|---|---|---|---|
| Administration of sterile distilled water only | 6 | 1.7 ± 0.3 | 2.3 ± 0.2 |
| Compound 5 (0.1 mg/kg) | 6 | 1.8 ± 0.4 | 2.5 ± 0.2 |

As is clear from Table 1, the osteomyelitis accompanying adjuvant arthritis was suppressed by all of the methanebisphosphonic acid derivatives (Compounds 1, 2 and 3). The osteomyelitis suppressing effect of the existing anti-inflammatory drugs (Compounds 4 and 5) was weak.

EXAMPLE 2

Suppression of Leukaemia Cell and Myeloma Cell Proliferation

Acute promyelocytic leukaemia cell strain KG-1, T-cell type acute lymphoblastic leukaemia cell strain RPMI-8402, B-cell-type acute lymphoblastic leukaemia cell strain CCRF-SB, chronic myelocytic leukaemia cell strain K562 and myeloblastoma cell strain ML-2 were prepared at concentrations of $2 \times 10^4$ or $4 \times 10^4$ cells per ml of culture medium. In each case, 0.05 ml quantities were added per well of a 96 well culture plate and culturing carried out at a carbon dioxide concentration of 5% for 24 hours at 37° C. Furthermore, 0.05 ml quantities of culture medium to which Compound 1 had been added were added to the aforesaid culture plate, and culturing carried out under the same conditions for 120 hours. The number of cells when the culturing was completed was calculated by the MTT calorimetric assay and the percentage suppression of tumour cell proliferation in terms of a control group to which no compound had been added was determined.

As well as Compound 1, there were used as test compounds 1-hydroxyethane-1,1-bisphosphonic acid disodium salt (Compound 6) and (4-chlorophenylthio)methane-1,1- bisphosphonic acid disodium salt (Compound 7). The results are shown in Table 2 as mean values±standard errors.

Using Dunett multiple comparison method (parametric), the results were assigned the symbol * when significant at a level of significance of p<0.05, and the symbol *** when significant at a level of significance of p<0.001, compared to the control group.

TABLE 2-1

Percentage suppression of KG-1 cell proliferation

|  | 10 mM | 100 mM | 1 mM |
|---|---|---|---|
| Compound 1 | −0.2 ± 3.9 | 44.2 ± 5.1*** | 97.8 ± 0.4*** |
| Compound 6 | 1.6 ± 2.1 | 2.9 ± 2.4 | 40.7 ± 1.7*** |
| Compound 7 | −1.1 ± 1.1 | 2.2 ± 1.6 | 97.1 ± 0.6*** |

TABLE 2-2

Percentage suppression of RPMI8402 cell proliferation

|  | 10 mM | 100 mM | 1 mM |
|---|---|---|---|
| Compound 1 | −5.9 ± 1.8 | 46.9 ± 2.0*** | 88.5 ± 1.1*** |
| Compound 6 | −3.4 ± 1.3 | 2.9 ± 1.5 | 28.2 ± 2.0*** |
| Compound 7 | −2.5 ± 2.0 | 7.4 ± 6.3 | 87.2 ± 0.6*** |

TABLE 2-3

Percentage suppression of CCRF-SB cell proliferation

|  | 10 mM | 100 mM | 1 mM |
|---|---|---|---|
| Compound 1 | 1.9 ± 2.0 | 14.4 ± 2.9*** | 71.6 ± 1.1*** |
| Compound 6 | 2.2 ± 0.8 | 0.4 ± 1.2 | 42.1 ± 0.9*** |
| Compound 7 | 0.1 ± 1.9 | 3.5 ± 2.2 | 61.3 ± 1.1*** |

TABLE 2-4

Percentage suppression of K562 cell proliferation

|  | 10 mM | 100 mM | 1 mM |
|---|---|---|---|
| Compound 1 | −1.9 ± 1.7 | 32.6 ± 2.0*** | 99.7 ± 0.3*** |
| Compound 6 | −2.5 ± 0.3 | 3.2 ± 0.6 | 44.4 ± 1.3*** |
| Compound 7 | −1.0 ± 1.3 | −3.1 ± 0.5 | 97.8 ± 0.3*** |

TABLE 2-5

Percentage suppression of ML-2 cell proliferation

|  | 10 mM | 100 mM | 1 mM |
|---|---|---|---|
| Compound 1 | 12.0 ± 7.3 | 72.0 ± 10.8*** | 156.6 ± 19.1*** |
| Compound 6 | −20.6 ± 17.2 | 16.0 ± 17.2 | 147.2 ± 20.4*** |
| Compound 7 | 7.3 ± 7.3 | 42.8 ± 10.1* | 130.4 ± 11.2*** |

As is clear from Table 2, the proliferation of tumour cells was suppressed by the methanebisphosphonic acid derivatives (Compounds 1, 6 and 7).

Industrial Utilization Potential

As shown in Example 1, it is clear that the methanebisphosphonic acid derivatives represented by general formula (I) relating to the present invention suppress adjuvant arthritis osteomyelitis while, in contrast, the osteomyelitis suppressing effect of existing anti-inflammatory drugs is weak. Furthermore, in Example 2, the methanebisphosphonic acid derivatives represented by general formula (I) showed a proliferation suppression effect in terms of various leukaemia cells. Thus, since the methanebisphosphonic acid derivatives represented by general formula (I) show an outstanding bone marrow abnormality therapeutic effect, efficacy can be expected in the prevention and treatment of osteoporosis, rheumatoid arthritis, multiple myeloma, osteomyelitis and other bone marrow diseases. Furthermore, application can also be expected in, for example, the prevention and treatment of hypoplastic anaemia, myelocytic leukaemia and other such haematopoietic disorders.

What is claimed is:

1. A method of treating patients with bone marrow abnormalities, comprising the step of:

administering an effective amount of a methanebisphosphonic acid derivative represented by formula (Ia),

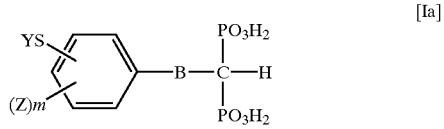

[Ia]

wherein, in formula (Ia),

B represents —X—$(CH_2)_n$—;

n is an integer in the range of 0 to 6;

X represents S, O, or NH;

Y represents a substituted or unsubstituted straight chain or branched chain lower alkyl, comprising 1 to 6 carbon atoms, wherein the substituents are amino, lower alkylamino, di-lower alkylamino or tri-lower alkylsiloxy, or substituted or unsubstituted phenyl, wherein the substituents are lower alkyl, lower alkoxy, lower alkylthio, trifluoromethyl, or halogen;

Z denotes a lower alkyl group, trifluoromethyl group, lower alkenyl, lower alkoxy, lower alkylthio or $C_{3-8}$ cycloalkyl; and m is an integer in the range of 0 to 2.

2. The method according to claim 1, wherein the methanebisphosphonic acid derivative is (4-methylthiophenylthio)methane-1,1-bisphosphonic acid.

3. A method of treating patients with bone marrow abnormalities according to claim 1, wherein the bone marrow abnormality is an inflammatory disease or haematopoietic disorder.

4. A method of treating patients with bone marrow abnormalities according to claim 2, wherein the bone marrow abnormality is an inflammatory disease or haematopoietic disorder.

5. The method according to claim 3 or 4, wherein the haematopoietic disorder is selected from the group consisting of osteomyelitis, multiple myeloma, hypoplastic anemia and myelocytic leukemia.

* * * * *